United States Patent
Benckini (10) Patent No.: US 9,265,750 B1
(45) Date of Patent: Feb. 23, 2016

(54) APPARATUS AND METHOD FOR CORRECTION OF ERECTILE DYSFUNCTION

(71) Applicant: Gene C. Benckini, Coopersburg, PA (US)

(72) Inventor: Gene C. Benckini, Coopersburg, PA (US)

( * ) Notice: Subject to any disclaimer, the term of this patent is extended or adjusted under 35 U.S.C. 154(b) by 0 days.

(21) Appl. No.: 14/531,160

(22) Filed: Nov. 3, 2014

Related U.S. Application Data (63) Continuation-in-part of application No. 12/930,512, filed on Jan. 10, 2011, now abandoned.

(60) Provisional application No. 61/338,666, filed on Feb. 22, 2010.

(51) Int. Cl.
| | |
|---|---|
| A61F 5/00 | (2006.01) |
| A61K 31/355 | (2006.01) |
| A61K 38/54 | (2006.01) |
| A61K 36/77 | (2006.01) |
| A61K 31/198 | (2006.01) |
| A61K 36/48 | (2006.01) |
| A61K 36/00 | (2006.01) |
| A61K 31/7048 | (2006.01) |
| A61K 36/185 | (2006.01) |
| A61K 33/30 | (2006.01) |
| A61K 35/32 | (2015.01) |
| A61F 5/41 | (2006.01) |

(52) U.S. Cl.
CPC ............... *A61K 31/355* (2013.01); *A61F 5/41* (2013.01); *A61K 31/198* (2013.01); *A61K 31/7048* (2013.01); *A61K 33/30* (2013.01); *A61K 35/32* (2013.01); *A61K 36/00* (2013.01); *A61K 36/185* (2013.01); *A61K 36/48* (2013.01); *A61K 36/77* (2013.01); *A61K 38/54* (2013.01); *A61F 2005/412* (2013.01)

(58) Field of Classification Search
CPC ............................. A61F 5/41; A61F 2005/412
USPC ...................................................... 600/38–41
See application file for complete search history.

(56) References Cited

U.S. PATENT DOCUMENTS

| | | |
|---|---|---|
| 3,631,853 A | 1/1972 | Burdette, Jr. |
| 3,744,486 A | 7/1973 | Wilson |
| 4,378,008 A | 3/1983 | Osbon, Sr. |
| 4,671,262 A | 6/1987 | West |
| 4,718,411 A | 1/1988 | Stewart |
| 4,741,329 A | 5/1988 | Marcune |
| 4,753,227 A | 6/1988 | Yanuck, Jr. |
| 4,856,498 A | 8/1989 | Osbon |
| 4,856,499 A | 8/1989 | Kelly |
| 5,095,895 A | 3/1992 | Walsh |
| 5,125,890 A | 6/1992 | Merrill et al. |
| 5,234,401 A | 8/1993 | Yamanaka |
| 5,421,808 A | 6/1995 | Osbon et al. |
| 5,462,514 A | 10/1995 | Harris |
| 5,624,378 A | 4/1997 | Baldecchi |

(Continued)

*Primary Examiner* — John Lacyk
(74) *Attorney, Agent, or Firm* — Sanford J. Piltch, Esq.

(57) ABSTRACT

An apparatus and method including herbal, amino acid, vitamin and mineral formulations for correcting and curing erectile dysfunction in men in order to create a natural erection. The formulations will assist in the correction and cure of erectile dysfunction along with the use of the vacuum apparatus to aid in the correction and cure resulting in the enhancement of the penis by clearing out any blockages and improving circulation to the male organ achieving greater overall length and girth of the penis for normal physical erections.

12 Claims, 6 Drawing Sheets

(56) References Cited

U.S. PATENT DOCUMENTS

| | | |
|---|---|---|
| 5,782,621 A | 7/1998 | Harris |
| 5,836,864 A | 11/1998 | Clark, Jr. |
| 5,910,316 A | 6/1999 | Keefer et al. |
| 5,951,460 A | 9/1999 | Vollrath |
| 5,964,695 A | 10/1999 | Vollrath et al. |
| 6,117,069 A | 9/2000 | Vollrath et al. |
| 6,277,062 B1 | 8/2001 | Vollrath et al. |
| 7,037,257 B1 | 5/2006 | Koenig et al. |
| 7,132,117 B2 | 11/2006 | Sambandan et al. |
| 7,186,213 B2 | 3/2007 | Osbon et al. |
| 8,137,262 B2 | 3/2012 | Osbon et al. |
| 2001/0044569 A1 | 11/2001 | Naghar |
| 2010/0221370 A1 | 9/2010 | Chan et al. |
| 2011/0040142 A1 | 2/2011 | Eum et al. |

APPARATUS AND METHOD FOR CORRECTION OF ERECTILE DYSFUNCTION

RELATED U.S. APPLICATION DATA

The present application is a continuation-in-part of U.S. application Ser. No. 12/930,512 filed on Jan. 10, 2011, which application claimed priority from U.S. provisional application No. 61/338,666 filed on Feb. 22, 2010.

BACKGROUND OF THE INVENTION

This invention resides in the fields of mechanical and herbal enhancement for erectile dysfunction. The present invention combines both mechanical and chemical stimulation to achieve physical erection of the male penis.

The inventor was stricken with both impotence and erectile dysfunction some years ago. Following recognition of the problems, the inventor researched and studied the various physical causes associated with the disorder. Based upon this research, he conceived of the idea of creating a vacuum pump that could perhaps stimulate the penis into an erection.

The research included a number of earlier issued patents, which were reviewed in detail, but which inventions failed to address the major problems with impotence and erectile dysfunction by presenting only an artificial erection and only a temporary solution to these problems. It is estimated that over ten million men suffer on a day to day basis from erectile dysfunction, i.e., failure to achieve an erect penis through a lack of blood flow to engorge the penis. This is not a psychological problem, but a physical problem with circulation of the male blood flow to the penis through the main arteries and veins of the organ.

Americans, however, are the real problem with what they eat. The consumption of all the junk foods in the markets and fast food restaurants with food processing and cooking with excessive fats and inexpensive frying oils, we are living in a junk food serving world for more than twenty-five, and possibly for fifty years. Common sense should tell people are becoming overweight and dying from heart attacks. Over many years plaque develops from eating the junk food which, in turn, is clogging the arteries and veins. This fact is clearly associated with the reduced blood flow to the penis, the penis is shrinking, the veins are shrinking, but men have associated this problem with age, which is totally wrong. The answer to cure and rejuvenate the erection of the penis is within reach, associated with a formulation to clean out the main arteries and veins. This is a wakeup call and people must educate themselves. It is ridiculous to go through life without a natural erection and the gratification of sexual encounters. These earlier patents only touch the surface of what could be reality with the correct formulation and the best invention ever to solve the problems associated with impotence and erectile dysfunction.

Yet millions of men out of desperation to have sex pay high prices for surgery, steroid injections and chemical enhancements. Many of these men end up with injuries and are totally disappointed. I have talked to many men over the last ten years who complain about herbal formulas that do not work. But from my research I found a different causation; I realized that the problem is internal and not external.

The following is a basic description of the internal structure of how the blood flows for natural erections. The dorsal artery which lies at the top of the penis and the deep vein that charges the corpora cavernosa and corpus spongiosum, which acts as a sponge, and the bulbourethral artery and vein on the bottom of the penis feed the corpus spongiosum to expand veins and arteries of the penis resulting in an erection for performance of the desired sex act. This would, of course, be a natural reaction for a healthy penis, but with clogged arteries and veins feeding the penis at only 35%-50% of the required blood flow, the male wants to have sex, but the physical organ is malfunctioning and the result is a failed erection. It will take years of sloppy eating habits and plain old ignorance to line your arteries and veins with plaque to cause the blockages resulting in reduced blood flow to the penis.

The average male will associate the problem of erectile dysfunction with age or psychological problems reasoning that most men are living with this condition and buying worthless hand operated penis pumps, some with constrictor rings, out of desperation. But one must realize as soon as the blood pressure from these artificial erections is released the penis becomes flaccid again and if the user keeps the ring on the base of his pressurized penis, how will an ejaculation occur? It is unimaginable trying to cope with this really excited and restricted penis. It must be painful and depressing when uninformed users having great expectations from these earlier devices fail for the reason that they do not resolve the initial internal problems. One should understand that this problem of erectile dysfunction occurring in a marriage might lead to divorce or betrayal, and for what, when the problem is clearly within reach with a little common sense.

At the advanced age of 65 years, I became a victim of this disorder and for over 10 years I got so mad at being worthless that I stopped dating. Every woman I knew wanted sex, but I took notice my penis started to shrink and the veins in my penis were shrinking away. The penis was useful for only a single function: urination. I started making excuses to cover up the problem, and I became significantly depressed and desperate. Wanting to overcome the problem I started to study the problem, researching and experimenting over 10 years.

There must be well over 50 devices available (or described in the research) based on substantially the same principles; vacuum pressure in a cylinder to suck blood into the penis. For what, the real problem has not been solved; only prolonged for the over ten million men who still suffer. The present invention will come to the aid of these men, because I know how difficult life can be when a man lives with his impotence and/or erectile dysfunction.

All of these earlier devices are basically using the same principles, ether manual or battery operated vacuum pumps, some with constrictor rings which are risky to use. Not one of these devices deals with the internal problems of impotence and erectile dysfunction or seeks to correct or solve the initial blockage and circulation of the arteries and veins by plaque. Of course a man cannot achieve an erection if his blood pressure is limited to 35%-50% of a strong flow. That's like trying to start an engine without gas. The earlier devices are failing to correct the initial reason that men cannot achieve a natural erection. We are in the age of modern technology, not the Stone Age, let's move on and help these ten million men who suffer from impotence and erectile dysfunction.

We need to eliminate the problems which are actually ruining these men's lives, their marriages, job attitudes at work, low self-esteem, embarrassment, and positive direction for the future. All these psychological results reflect on the suffering male; a man must be a man and that includes getting a natural erection, not a temporary solution to an ongoing problem. Believe me I know; I have been down this path to depression and despair. I was sick of the entire problem and I not only cured and corrected my problem, but I ended up achieving an erect penis following the tenets of the present invention.

The research began with a low volume pressure pump which was disassembled to convert the valves from their original purpose to blow low pressure air into aquariums by reversing the air flow of the valves from air pressure output to vacuum intake. But the vacuum intake only reached 2.5 inches Hg. In order to increase the vacuum pressure the windings on the motor coil were increased by adding wire revolutions until the vacuum was built up to 8.5 inches Hg. The next alteration was to increase the power of the magnets on both sides so that the draw of the magnets was increased. Following that was to increase the size of the vacuum line. Originally the pump had a ¼" short line for vacuum which exhibited very little vacuum or suction. But with the change of the motor characteristics and increased magnetic power for the diaphragms, when a 10" long clear acrylic tube with a 2" internal diameter was installed on the vacuum side of the pump, the tube created a much greater volumetric space for the exertion of the increased vacuum pressure of up to 8.5 inches Hg. Upon placing a flaccid penis into the tube using a little lotion and following a 30 minute exposure to the repeated vacuum pulls of the pump, the penis was removed exhibiting a greater length and girth. Although the penis was elongated, it still remained limp. Of course a man cannot have intercourse with a limp penis. Additional research was needed to understand ways to make the penis more rigid. An understanding had to be reached to create an engorged penis instead of a balloon half full of air. The realization was that by analytical reasoning with no air in a balloon, therefore there was no blood pressure in the penis.

Notice was taken that the penis had originally shrunk and the veins had almost disappeared from external view. The conclusion was made that the arteries and veins must be clogged with plaque built up over many years, as time has taken its toll on man. Research was begun on clog busters and a formula was derived to reduce plaque formed in the arteries and veins. A program using the formula was begun to clean out the arteries and veins to last one full month. However, after 2 to 3 weeks of treatment with the formula, the subject could feel the penis getting longer and fuller with the penis veins becoming much more vivid to the eye. The subject waited the full month and then initiated step 2 of the process by employing the vacuum pump apparatus to help expand the penis cells and dorsal artery, along with the bulbourethral artery, which would in turn expand all the penis veins and assist with greater blood flow into the arteries and veins. The second step of the process took 30 minutes of treatment and the subject could feel some enlargement of the penis as it was being pulled into the cylinder. After 30 minutes of treatment the penis had become engorged and filled the cylinder. It was estimated that the penis was experiencing over a 60% erection and had increased elongation and girth. The preliminary results showed that the corrective process was on the right track. All that was needed was to remain with the research program. Although the accomplishment of correcting impotence and erectile dysfunction was proceeding, there was still an additional step needed. Another formulation still was needed to boost the erection process and to be able to obtain a natural erection when needed. The penis must be itself without any constrictors, no artificial erections, no trying to pull off constrictor rings with the penis in the excited mode.

The additional formulation was determined through trial and error and has been determined to be a number of vitamins coupled with a number of herbal formulations and minerals that are to be ingested on a daily basis for 30 days, once or twice daily. This second formulation will assist in the enlargement of the penis arteries and veins such that any blockages are removed, the musculature is rejuvenated over time and nitric oxide is reintroduced in sufficient quantity to assist with an erection.

It is, therefore, one object of the present invention to systemically rejuvenate the arteries and veins through the reduction or elimination of plaque deposits within the vessels by use of preparatory and maintenance formulations to naturally assist in an erection of the male genital organ. It is also an object of the present invention for the preparatory formulation to help dissolve any plaque build-up in the blood vessels over years of poor eating habits and open the arteries and spider veins of the penis to rehabilitate those vessels to accommodate the required blood flow to the penis and eliminate "erectile dysfunction" problems in the future. It is a further object of the present invention to provide a vacuum pump for enlarging the penis that is designed with an appropriate and safe vacuum pressure for the very best natural results in building a stronger erection with greater length and girth for a very natural erection to correct erectile dysfunction for future sexual satisfaction. It is a still further object of the present invention to provide a vacuum pump having a simple mechanism to regulate and maintain the desired vacuum pressure, without any substantial fluctuation, to achieve the very best penis enlargement while eliminating problems associated with prior pumps that can require a pressure gauge and valve to manually regulate and maintain the vacuum pressure. It is also a further object of the present invention to completely eliminate the dangerous restrictor rings, clamps and straps that can prevent any possibility of ejaculation release that can be painful and unhealthy. Constrictor rings, clamps and straps are designed only for an artificial erection with use recommended for no more than 30 minutes and have no place for use with the present invention.

It is yet a further object of the present invention to provide a natural stimulus so that the use of the preparatory and maintenance formulations will almost double the size of the penis in length and girth by having a resultant effect on the penis anatomy. This is accomplished by stimulating the corpora cavernosa and the corpus spongiosum of the male penis through the use of the combination of herbs, vitamins and minerals over a predetermined period of time followed by the use of the vacuum pump that will increase both the length and girth of the penis. In addition the users testicles will increase proportionately in size and circulations into and through the penis will be much stronger. It is still another object of the present invention to provide a vacuum pump that has a built-in pulsation action to help with development of the penis size. It is also another object of the present invention to provide a treatment tube in the form of an elongated transparent cylinder with a double roll over flange at its open end for creating a smooth vacuum seal against the user's body for sealing off ambient air for the best results.

Other objects will appear hereinafter.

SUMMARY OF THE INVENTION

The inventor created this invention system for himself. Of course, the inventor was inflicted with the condition of impotence and erectile dysfunction for years before he was able to prefect the formulations and pump apparatus to be able to correct the male genital malfunction on his own.

The first formulation was created to clean the veins and arteries of the male genital organ so as to start functioning normally. The vacuum pump apparatus was designed to help and, in conjunction with the first formulation, to place a vacuum on the organ by use of a clear rigid cylinder with the idea of expanding the arteries and veins while slowly forcing blood through the structure of the male organ. The results of this trial worked well; the organ became much bigger in length and girth; but with no spine. It was thought that since the genital organ was in a dormant stage for years the organ needed to rebuild its stamina. With this idea in mind, the second formulation was created to build-up nitric oxide levels and testosterone to regain the strength and endurance needed to maintain a natural erection without useless manual pumps and constrictor rings to force the blood to remain in an artificially erect penis.

A method is described for enhancing penile hemodynamics in humans by increasing the capacity for a natural erection of the male penis that comprises the following steps. A preliminary formulation of herbs and vitamins is ingested daily for at least a thirty day period to increase the blood flow into and through the male penis by reducing plaque deposits and inflammation of the vessels. Following the initial thirty day period, a vacuum pump having an elongated open-ended cylinder for creating a vacuum over and along the exterior of the male penis is utilized to assist in the enlargement of the penis through the engorgement of the blood vessels of the penis by increased blood flow. Simultaneously with the use of the vacuum pump, a second or maintenance formulation of a selection of herbs, an amino acid, a vitamin, and a mineral is ingested daily to maintain the increased blood flow into and through the male penis, to increase the nitric oxide levels within the human body, to stimulate penile erections, and to rejuvenate and enhance muscle growth and strength of the male penis.

The preliminary formulation consists of a vitamin for reducing plaque buildup in blood vessels, a first herb for reducing fibrinolytic and antithrombic conditions in the human circulatory and musculature systems, a second herb for assisting against inflammation of blood vessel walls, accompanied by appropriate amounts of water to aid in the dispersal of the formulation throughout the human body. The second or maintenance formulation consists of an amino acid, a first herb, and a mineral to assist the human body in manufacturing nitric oxide, at least five selected herbs for rejuvenating and enhancing muscle growth and strength and increasing testosterone level, and a vitamin to continue preventing the build-up of plaque that was previously reduced in the blood vessels.

BRIEF DESCRIPTION OF THE DRAWINGS

For the purpose of illustrating the invention, there is shown in the drawings forms which are presently preferred; it being understood, however, that the invention is not limited to the precise arrangements and instrumentalities shown.

DETAILED DESCRIPTION OF THE PREFERRED EMBODIMENTS

The following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

Figure 1:
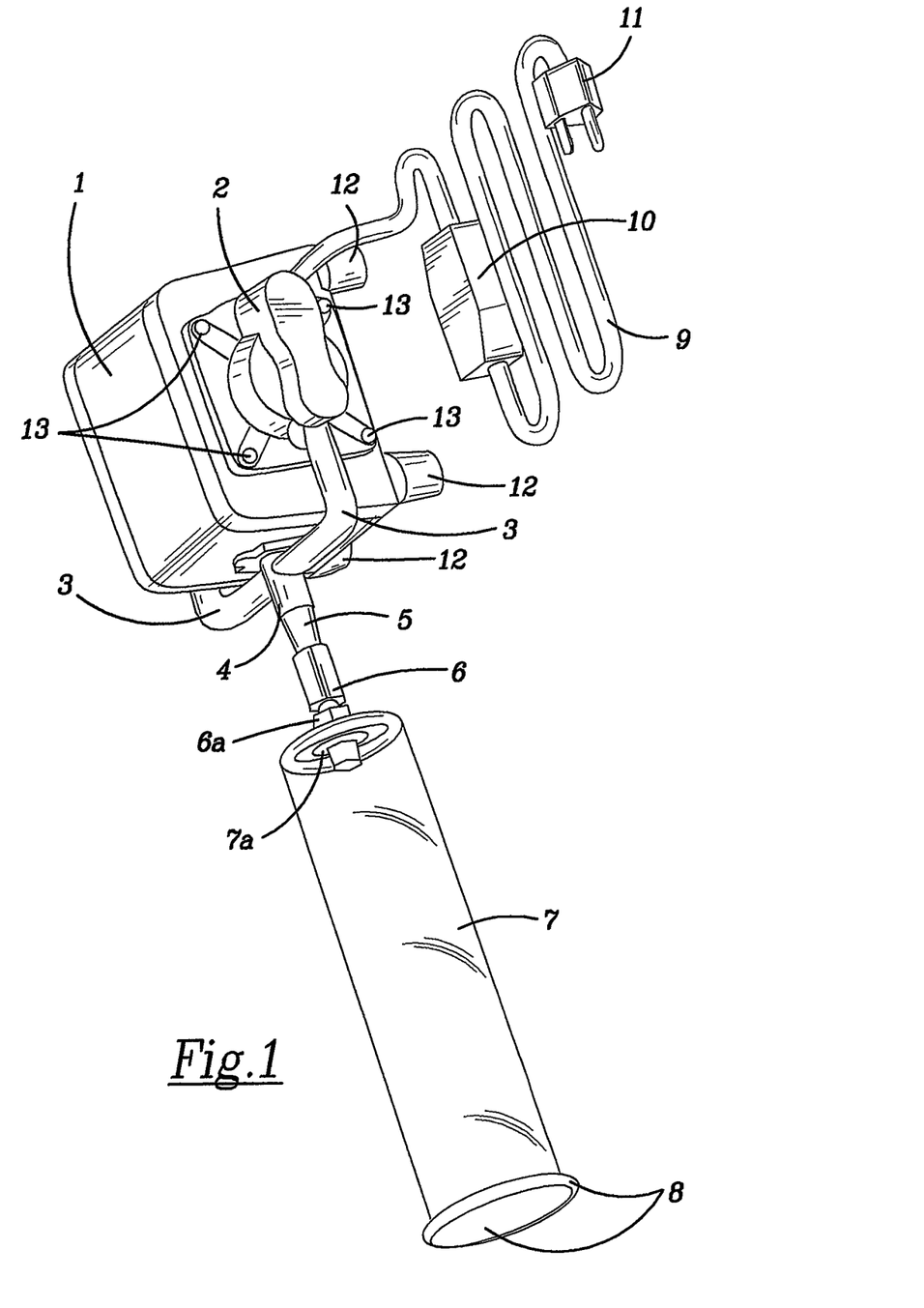
FIG. 1 is a perspective view of the vacuum pump housing and associated tubing, an associated elongated cylinder for housing the male penis while in use and the control and power cord of the present invention.

Referring now to the drawings in detail, where like numerals refer to like parts or elements, there is shown in FIG. 1 the main body or housing of the vacuum pump 1 which operates without any lubrication and functions with electrical power to activate the internal magnetics. Dual vacuum valve housing units 2 that are activated by both magnetic plates is internally set to control the vacuum pressure by the mechanism. Diaphragm vacuum pump dual intake lines 3 on both sides equalize the vacuum pressure evenly to each pump. A T-bar connector 4 attaches to each of the dual vacuum intake lines 3, which are attached to the diaphragm housing. At the distal end of the T-bar 4 is a threaded nipple 5 connecting the T-bar to a double threaded female adaptor 6 that is, in turn, connected to a through fitting 6a allowing fluid (air) flow through the treatment cylinder backing plate 7a. An elongated transparent rigid treatment cylinder 7, measuring nine and one half inches in length with a one sixteenth inch outer wall for durability and to prevent cracking or breakage is connected to the fluid path fittings through its back wall plate 7a. The treatment cylinder 7 has an internally smooth surface to receive the male organ for the treatment process and a smooth portal double roll-over flange 8 for safety and ease of use. The treatment cylinder 7 has a seven to eight inch internal length dimension and up to a three inch internal diameter for various male organ sizes in a flaccid stage for the development process of the male organ.

The vacuum pump 1 is powered through a grounded electrical connection cord 9 having an inline electrical on/off switch 10 for the users that is within reach of the pump 1 terminating in a the three prong electrical plug 11 for grounded outlets. The vacuum pump 1 is housed within a vacuum pump housing with four bolted runner booties 12 located at each of the lower corners to control and direct the building pulsation action directly to the elongated cylinder, which in turn stimulates the development process of the male organ. Four bolts 13 at each corner of the vacuum valve housing are utilized to stabilize and quiet the pulsation action of the pump 1.

Figure 2:
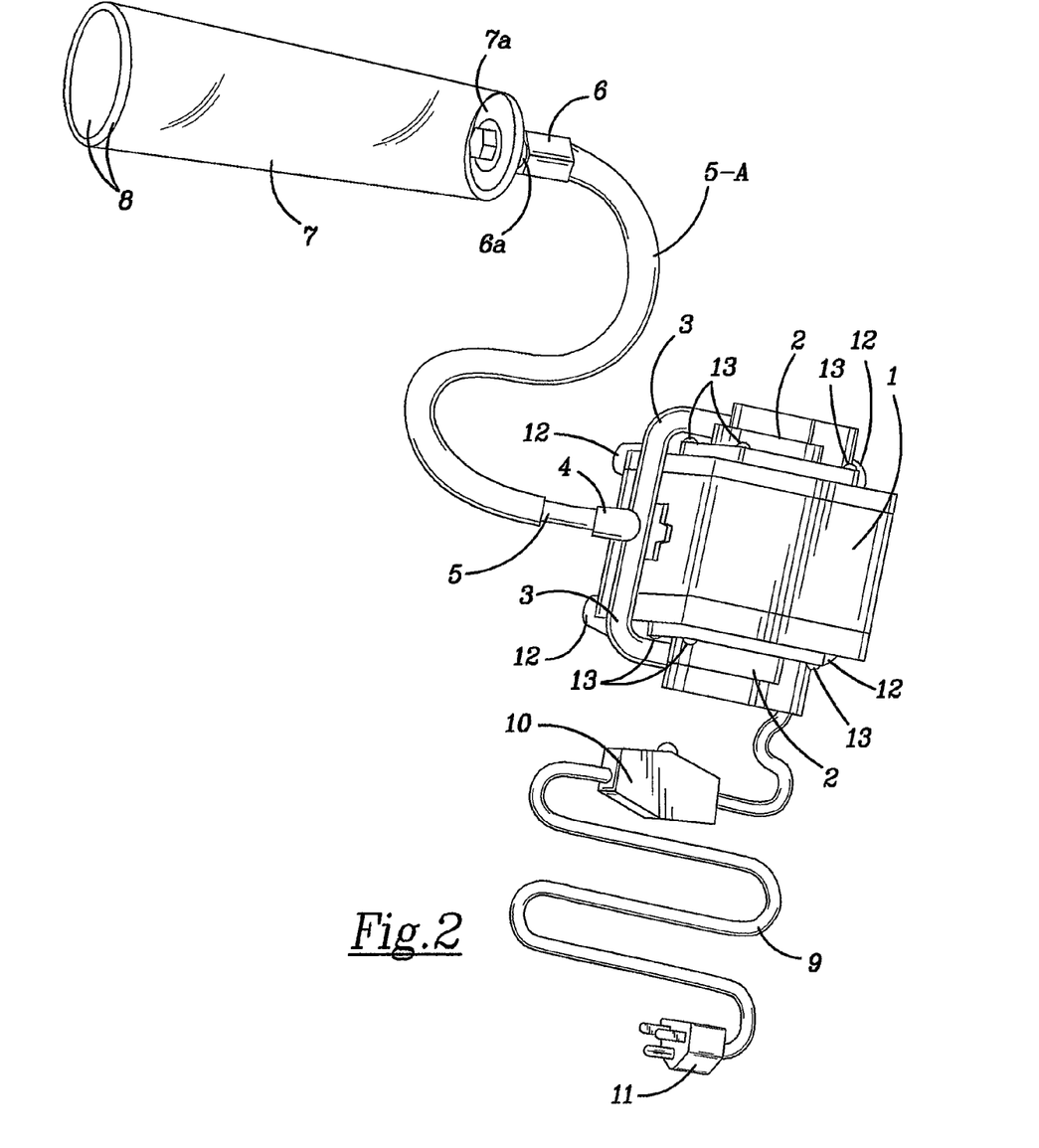
FIG. 2 is plan view of the vacuum pump housing and associated tubing, an associated elongated cylinder for housing the male penis while in use, and the control and power cord of the present invention.

FIG. 2 shows substantially the same configuration of elements for the vacuum pump 1 as does FIG. 1 but from a different perspective. The significant difference is the elongated flexible tube 5a connected between the threaded nipple 5 and the threaded female adaptor 6 creating an extended space between the vacuum pump 1 and the treatment tube 7. The elongated flexible tube 5a is preferred to be approximately six feet in length and one half inch in diameter and have sufficient flexure so as not to kink or otherwise impede fluid flow. The elongated flexible tube 5a is provided for the convenience of the user so as to position the vacuum pump 1 at a distance from the treatment tube 7 and to provide for greater privacy if desired. With an increased length tube 5a, the vacuum pump 1 may be placed at a distant location in a home, such as another room, or in a cabinet with sufficient space to house the vacuum pump 1 and run a half inch rigid plastic line from the pump location to the treatment location for convenience and privacy of use without the need to ever hear the vacuum pump operating. There is no loss of vacuum pressure over a limited distance so that the vacuum level remains precisely the same through the entire development of the male organ.

Figure 3:
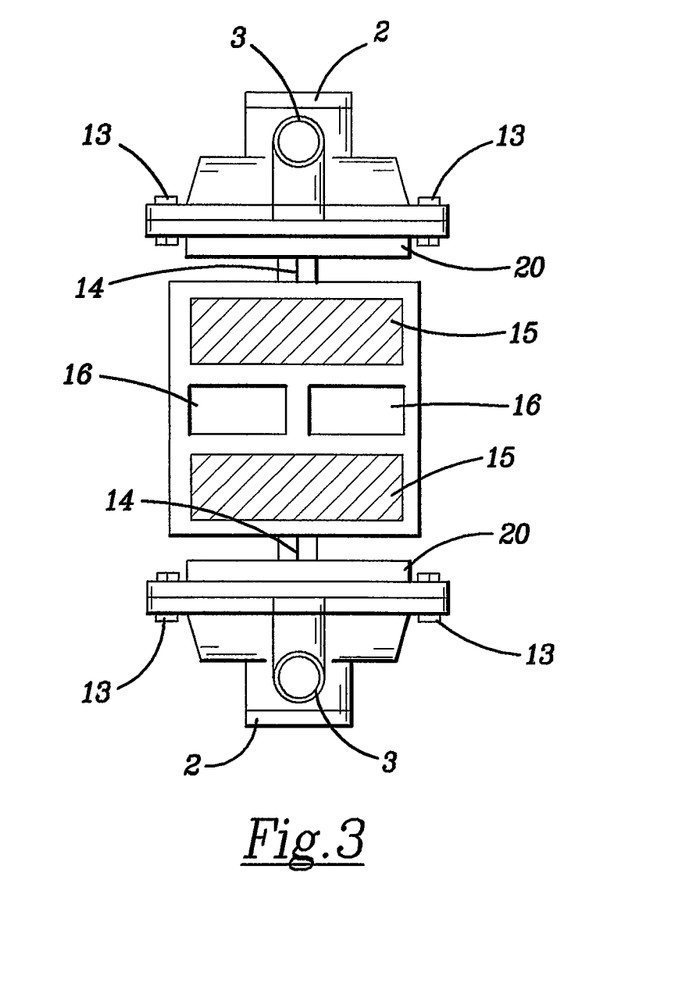
FIG. 3 is a sectional view of the dual air valve housings of the vacuum pump which contain two separate vacuum valves of precisely the same vacuum air pressure of the present invention.

FIG. 3 shows the dual air valve housings 2 which contain two separate vacuum valves for creating precisely the same vacuum pressure. The valve portals 3 of the vacuum pressure valves receive the air lines on both sides directly from the T-bar connector 4 which is bolted to the center of the pump housing to stabilize the vacuum lines. Bolts 13 on all four corners of both dual valve housings are provided to stabilize and seal off low level noise. Dual electromagnetically activated ⅛"steel rods 14 are connected to the internal magnetic plates and are forced to move at a rapid pace, but in only ¼ inch long reciprocal movements to create the vacuum pressure. Dual heavy duty magnetic plates 15, wrapped in very finely coiled wire are an intricate part of the vacuum air stabilizing feature which regulates the vacuum pressure to both valves. The magnetic plate housing 16 is molded around both of the electromagnets 15 with the fine coiled electrical wire and also supports the steel rods 14 fast and short reciprocal movement at their rapid pace. Separating the electromagnets 15 from the vacuum valves are dual diaphragm backing plates 20 that bolt to the vacuum housing and incorporate soft rubber membranes that are used to synchronize the vacuum pressure that remains unchanged throughout the process.

Figure 4:
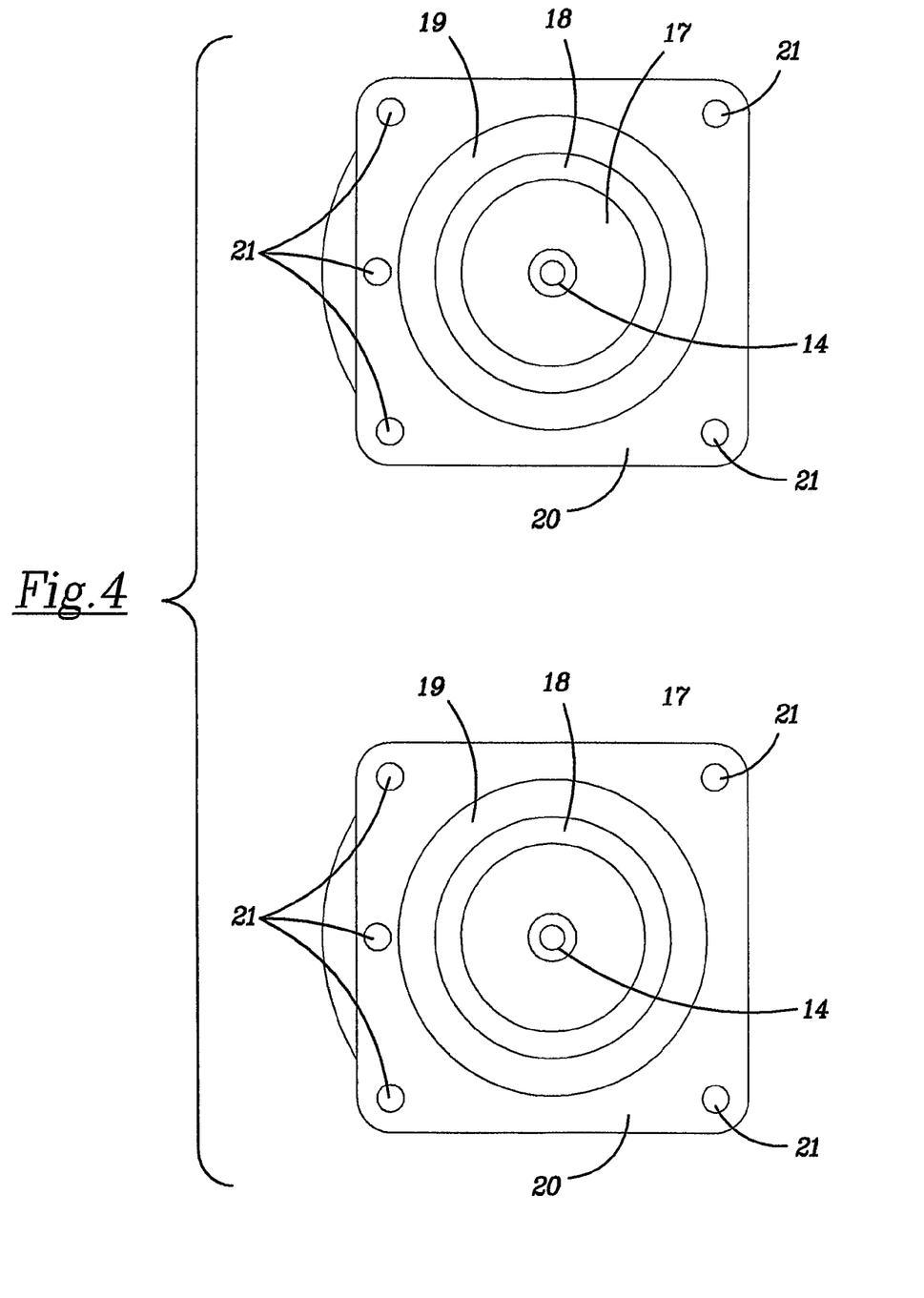
FIG. 4 is a plan view of each of the membrane housings of the vacuum pump of the present invention.

FIG. 4 shows the operative elements of the right and left side vacuum valves of the vacuum pump 1. At the center of the vacuum valves are the distal ends of the ⅛"steel rods 14 extending outward from the electromagnets 15 that operate the internal and external membranes and valves. A plastic disk 17 covers and supports the rubber membranes 18 of the dual vacuum air intake created by the very rapid reciprocal movements of the steel rods 14. Dual rubber disk-like membranes 18 are positioned between the plastic disk 17 and the dual diaphragms 19. Dual backing plates 20 bolt each of the vacuum valves to the vacuum pump housing. Four bolt holes 21 on the dual backing plates 20 are used for bolts 13 to fasten the vacuum valves to the pump housing.

Figure 5:
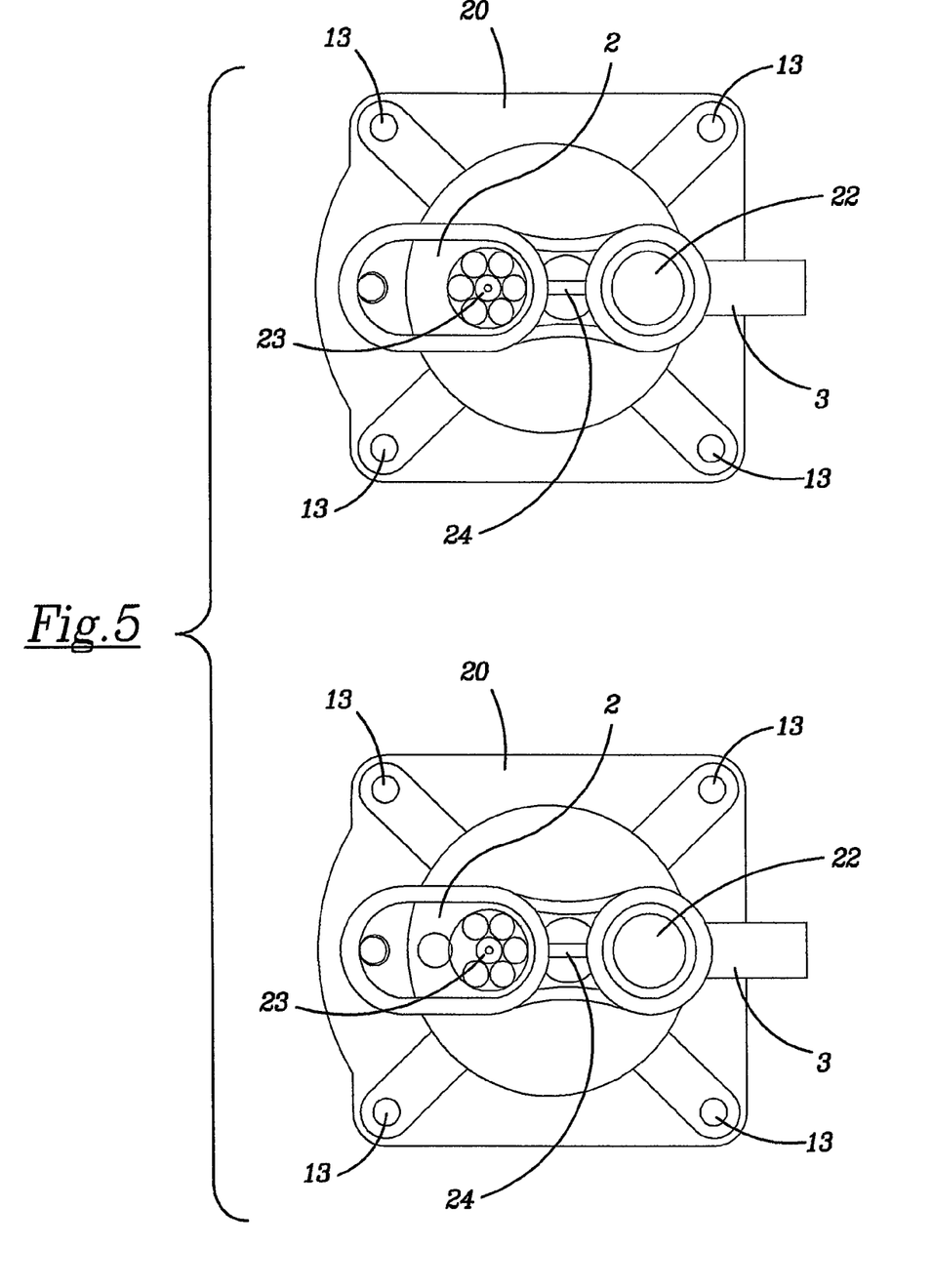
FIG. 5 is a plan view of the dual valve housings on each side of the diaphragm vacuum pump of the present invention.

FIG. 5 shows the left and right side the valve housings 2 on each side of the vacuum pump 1. Dual vacuum intake ports 3 connect to each of the dual vacuum valves of the pump 1. The dual backing plates 20 encompass, and with the valve housings 2 cover the internal membranes 18 and diaphragms 19 and are fastened to the main housing body with bolts 13 in each of the four corners of the dual valve housings 2. Dual vacuum air valves 22 synchronize the vacuum intake air on both sides of pump 1 to properly create the internally designed vacuum pressure that is applied through the elongated treatment cylinder 7 to an inserted male genital organ. Dual diaphragm relief valves 23 maintain equal vacuum pressure to the dual vacuum valves as a backup feature. To prevent interruption or variation of the vacuum pressure due to fouling of the vacuum valves, dual filter inserts 24 collect any dust and also provide access to a stroke path adjusting nut (not shown) on the steel rods 14 of the pumping mechanism that operates the plastic disk 17 and the rubber membrane 18 of the vacuum valves.

Figure 6:
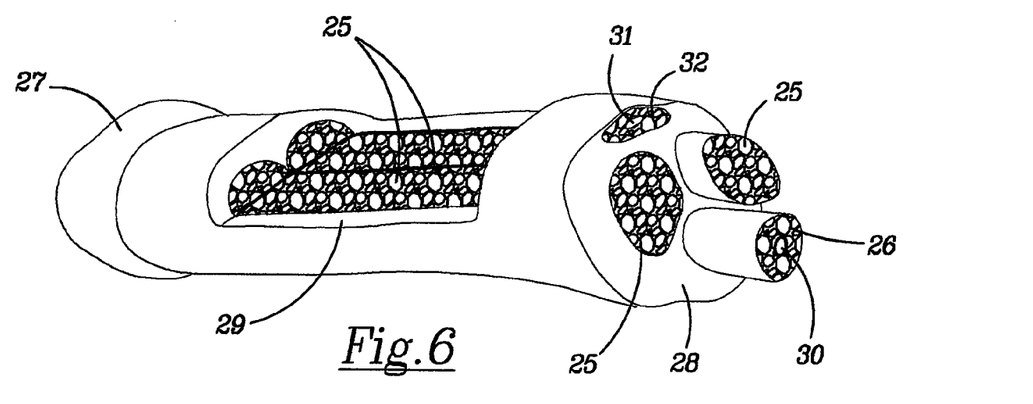
FIG. 6 is a perspective cutaway view of a human male penis.
Figure 6A:
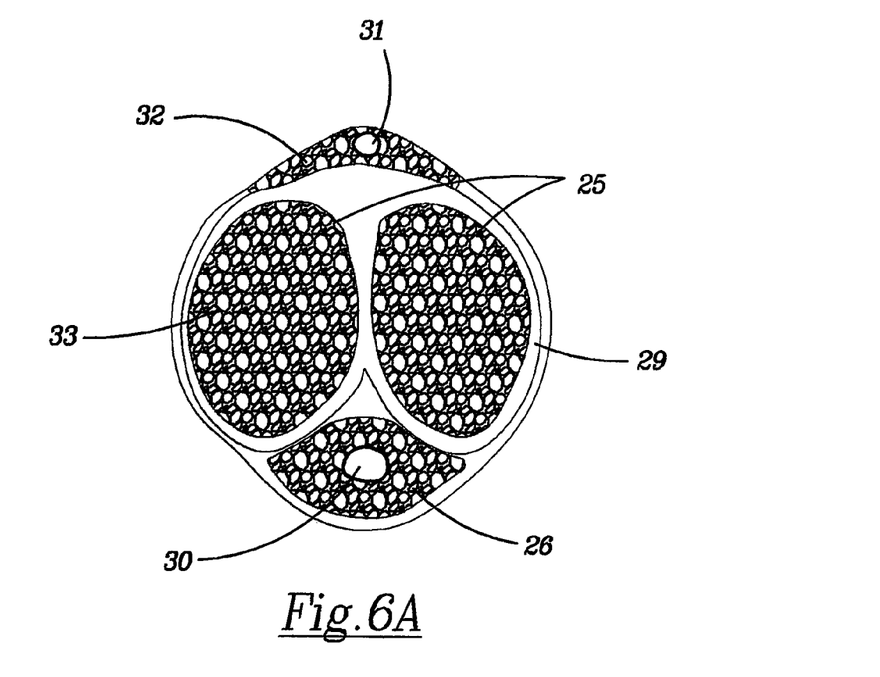
FIG. 6A is a sectional view of a human male penis.

There also needs to be an understanding of how the apparatus functions to assert its effect upon the human genital organ. To reach this understanding FIGS. 6 and 6A show cutaway and sectional views, respectively, of the male genital organ, i.e., the penis or glans. In the vast chambers of the penis that make up the corpora cavernosa 25 and the corpus spongiosum 26 there is clearly shown literally thousands of cells and other tissues that make-up the entirety of the penis which all must function in harmony in order to achieve a full and natural erection. The corpus spongiosum 26 has its own chambers of cells and tissues that expand under the advent of normal blood pressure, but in reality and tests, experiments time after time have proven that the user will get the same size erection every time, simply because the user only has the same blood pressure to expand the cells and tissues to the same limited degree.

Tests performed with the described apparatus, using precisely and exactly the right vacuum pressure to bring forth the greatest potential degree of expansion to the corpora cavernosa 25 and the corpus spongiosum 26 and the glans head, increased the penis length and girth by 35% to 60% of its original size before treatment. The glans (penis) head 27 is usually limited to its same or normal size during an erection until treatment of the glans with the described apparatus that may well cause almost doubling the size of the penis head 27 for more pleasure for the female in stimulating her vaginal canal. Further, the additional length and girth of the penis will place more pressure on the female clitoris and with the increased length of the penis it may extend up into the uterus resulting in additional climaxes. The other physical attributes of the penis are the outer shield of expansible skin 28 which encases the corpora cavernosa 25 and the corpus spongiosum 26 and protects the cells and tissues from exterior injury. The tunica albuginea 29 is a strong inner shield surrounding the corpora cavernosa that also expands like an inner-tube of a bike tire as it protects the complex genital organ from injury and like the air in the inner-tube it expands with additional blood pressure to yield to a higher degree of expansion. The urethra passage 30 for urinary tract discharges should remain unblocked to keep the prostate gland healthy. The dorsal vein 31 is very important to deliver blood to all the spider veins in the genital organ that contribute to the harmony of the erection with the arteries. The dorsal artery 32 rises and expands with the sexual excitement to feed the corpora cavernosa 25 and the corpus spongiosum 26 to the degree of vacuum pressure delivered to the treatment tube 7 of the apparatus. Increased blood flow in the penis is indicated by the circle 33 on the left side of the penis in FIG. 6A.

The preparatory formulation to begin the removal of any blockages in the arteries and veins of the human subject, and particularly the veins and arteries supplying blood flow to the male genitalia, i.e., the penis, is described below. The formulation should be used for at least a 30 day regimen leading up to the treatment with the described apparatus.

(1) One capsule 400 IU of vitamin E taken daily in the morning and one capsule 400 IU vitamin E taken daily in the evening every day for 30 days for a total of 800 IU/day.

Vitamin E is included as it has an effect on the human body that may reduce or eliminate the buildup of plaque in blood vessels resulting in greater blood flow and strength of flow. As vitamin E has the effect of reducing plaque buildup in blood vessels, it has been suggested to have therapeutic effects for male infertility with a suggested dosage of 200-600 IU daily. However, there is no linkage known to the inventor that vitamin E has been found effective in permitting increased blood flow to and through the male genital organ until now.

(2) Take two capsules of triple strength nattozimes 195 mg. daily in the morning and two capsules daily in the evening after meals for a total of (4) capsules per day.

Nattozimes is a proteolytic system from *Aspergillus oryzae* that is a substitute for nattokinase in dietary supplements used for cardiovascular or anti-inflammatory support. Nattokinase is a subtilisn-like protease produced by *Bacillus natto* and has properties that closely resemble plasmin and readily digests plasmin, fibrin and similar synthetic substrates. The nattokinase activity of the proteolytic system is to hydrolize the peptide linkages of standard fibrin substrate. The primary usage is to treat fibrinolytic and antithrombic conditions in the human circulatory and musculature systems. However, a little known suggested use, when poor circulation is indicated, is to reduce increased fibrin in blood vessels that could be a source of a lack of proper blood supply to the male penis causing male erection issues.

(3) Take two 200 mg. capsules of horse chestnut (*Aesculus hippocasatanum*) daily, one in the morning and one in the evening.

The seed of the horse chestnut tree is used to produce 20% aescin which is used primarily for its venotonic effect for vascular protection and anti-inflammation. It is not known for use with any male erectile dysfunction or human circulatory disorders.

(4) Take one to two table spoons of apple cider vinegar per day with meals; recommended as a salad dressing.

One should switch salad dressings with high cholesterol ingredient concentrations to regular use of apple cider vinegar (5% acidity) with all salads for the rest of your life. This will keep you healthy and it is quite useful in clearing the plaque in the arteries and veins.

(5) Drink plenty of water when ingesting triple strength nattozimes and horse chestnut capsules; a 120 lb. person should drink 60 oz. of water a day, or a 200 lb. person at least 90 oz. of water per day.

The vitamin E, nattozimes and horse chestnut formulations are intended to reduce any blockages (plaque) formed in the human vascular system and to maintain those vessels as open as possible. The substitution of the apple cider vinegar for any manufactured salad dressing is intended to reduce consumption of fats, sugars, cholesterol and sodium that will likely result in plaque build-up in circulatory vessels. The inventor is 75 years old and this formulation works well for him. The veins and arteries of the penis start to increase in size, which means the formulation is working and you feel more energetic.

The second or maintenance formulation should be used in conjunction with the use of the described apparatus to enhance the enlargement and rejuvenation of the male genital organ. The formulation is described as follows.

(1) One should take by mouth 3-6 grams of L-arginine daily, e.g., 3000 mg. in the morning and 3000 mg. in the evening, since the evening time is when the pituitary gland stores hormones that react directly to the sexual excitement of the male and then to the genital organ for erection.

Arginine is an amino acid usually obtained from high protein containing foodstuffs such as red meat, poultry, fish and dairy products. Although primarily used for treating heart and blood vessel conditions, arginine has been suggested for treating male erectile dysfunction. Arginine is used to supplement naturally formed amino acids and assist the body in synthesis of nitric oxide.

(2) Take 3 grams of L-Citrulline daily, e.g., 1500 mg, in the morning and 1500 mg in the evening to supplement the production of the amino acid from arginine.

Citrulline is an amino acid made from omithine and carbamoyl phosphate in one of the central reactions of the urea cycle in the body. It is also produced from arginine as a by-product of the enzymatic reaction of trichohyalin at the inner root sheath and medulla of hair follicles. Arginine is first oxidized into N-hydroxyl-arginine, which is then further oxidized to citrulline concomitant with the release of nitric oxide. Supplementation of citrulline, along with arginine, may reverse penile endothelial dysfunction correcting one cause of erectile dysfunction and acts to aid the natural synthesis of nitric oxide enhancing penile erection.

(3) Take one *Butea superba* 500 mg. tablet in the morning and one in the evening after meals.

*Butea superba* is a plant that grows in southern Asia in the countries of India, China, Thailand and Vietnam and is thought to be an aphrodisiac used to improve sexual function. Although it is known that people have taken this herb to help treat male erectile dysfunction, there is only anecdotal evidence to show complete effectiveness, either alone or in combination with other supplements, indicating significant improvement in male erectile dysfunction. This herb is primarily used by the inventor for rejuvenating the penis and also human well-being for additional strength and energy.

(4) Take 800 IU of vitamin E per day, one 400 IU dose in the morning and one 400 IU dose in the evening after meals.

Vitamin E treatment is continued as it has the effect on the human body for reducing or eliminating the buildup of plaque in blood vessels resulting in greater blood flow and strength of flow. The continuing dosage of vitamin E has a maintenance effect on the circulatory system to prevent the build-up of plaque that was previously reduced.

(5) Take two capsules of *Catuaba* bark [465 mg.] in the morning and 2 capsules in the evening to help the size of the penis.

*Catuaba* is an infusion formulated from the bark of a number of trees harvested in their native Brazil. *Catuaba* bark and preparations containing the formulation are used as aphrodisiacs, to heighten sexual arousal, and as supposed remedies for male sexual performance problems. However, there is only anecdotal evidence that *catuaba* has any effect on male sexual performance and, if it does, exactly what that enhancement might be. *Catuaba* is used by the inventor for assisting in stimulating an erection.

(6) Take 500 mg. of Icariin extract 40% twice a day; once in the morning and once in the evening.

Icariin is a flavonol glycoside derived from several species of plants belonging to the genus *Epimedium*, Berberidacee, which are commonly known as Horny Goat Weed. Extracts from these plants have been known to produce aphrodisiac effects and are commonly used in Chinese herbal medicine to enhance erectile function. It is thought that icariin is likely to be the primary active component of *Epimedium* extracts as it has been shown to share several mechanisms of action with compounds used in Western medicine to treat impotence and improve sexual function. Icariin has been found to enhance the production of bioactive nitric oxide as well as mimicking the effects of testosterone. While icariin has been shown to improve penile hemodynamics in rats, no human trial reports are presently known. Icariin is used to enhance the synthesis of nitric oxide within the body. The inventor's experience using this herb shows that it enhances erections and also assists the body building of muscles and strength.

(7) Take two capsules of *Tongkat ali* extract 1:200 [300 mg.] in the morning and another two capsules in the evening.

*Eurycoma longifolia* (commonly known as *tongkat ali*) is a flowering plant in the family Simaroubaceae native to Indonesia, Malaysia, Thailand, Vietnam and Laos. A water-based extract of the plant has been patented by the Malaysian government and the Massachusetts Institute of Technology citing a use for sexual dysfunction and male infertility, i.e., testosterone enhancement and sperm mobility and motility. A polar organic solvent derived from the plant has also been described in a patent application publication with similar claims for enhancing testosterone. These known uses to enhance low testosterone or to enhance sperm mobility and motility are significantly different that the use described herein to build the size of the penis and for body building of muscles.

(8) Take one capsule of *Tribulus terrestris* [500 mg.] in the morning and one capsule in the evening.

*Tribulus terrestris* is a taprooted herbaceous perennial plant in the Caltrop family that grows as an annual in colder climates and is an herbal nutritional supplement that is promoted to produce large gains in strength and lean muscle mass. Although there is some indication that is may be successful in body building and increasing the body's natural testosterone level, no definitive clinical trials are reported. This is quite different than the intended use for building blood circulation and enhancing erections and body building of muscles.

(9) Take 75-100 mg. of Zinc per day to help build up the nitrate oxide levels.

Zinc is an essential mineral that is naturally present in some foodstuffs and also available as a dietary supplement. Low zinc levels in humans have been associated with male infertility, but there is insufficient clinical evidence that supplementing zinc is effective in improving male sexual problems. There is no indication from earlier sources that zinc has been used to enhance nitrate oxide levels in humans, and without significant levels of nitric oxide there will be no penile erection.

(10) Take two capsules of Velvet Deer Antler [500 mg.] per day; one in the morning and one in the evening.

Deer velvet antler can be divided into sections, each of which is used for different medical purposes in traditional Chinese medicine. Deer velvet is used to boost strength and endurance, improve the way the human immune system functions, counter the effects of stress, and promote rapid recovery from illness. Some people have used deer velvet to increase levels of certain sex hormones (estrogen and testosterone), improve fertility, increase interest in sexual activity, and treat male sexual performance problems. However, there is only anecdotal evidence of any success in treating male sexual problems, especially those related to erectile dysfunction. The present use is to create a powerful rejuvenating effect for sexual functioning, increased testosterone, and higher energy levels.

This combined formulation of amino acids, vitamin, mineral and herbs will slowly take over your life without you even thinking about it. Just like a blood transfusion, your body will start to feel stronger, more energetic, with more endurance for sexual performance. Your many aches and pains will slowly weaken and some will disappear. Your attitude will slowly change. You will be more considerate, more polite, and you will find yourself laughing to yourself and smiling. You will find smiling to other people easier. It just takes over your life for well-being and health. You will also start to look younger and you will visually see the difference in six months.

Following the recommended time period for the continuing dosages of the preparatory formulation, the user can begin use of the vacuum pump apparatus in conjunction with the maintenance formulation. Operation of the vacuum pump apparatus is described as follows. Place the diaphragm pump on a rigid level surface plugging the electrical cord into a grounded electrical outlet. Take the elongated transparent cylinder and attach it to either the flexible hose or directly to the pump. If using the flexible hose, the other end of the hose should be attached to the pump. Apply a sufficient amount of lotion with aloe vera to the male genital organ (penis) or place a thin layer of the lotion inside the cylinder spreading it evenly over the internal surface. Now you are ready to insert the flaccid or semi-erect penis into the opening of the cylinder with flange surrounding the opening of the cylinder making contact with the user's torso. Turn on the vacuum pump with the inline switch and the diaphragm pump will slowly pull the penis into the cylinder all the way in to the very base of the penis so a tight seal is made between the user's body and the cylinder. Allow approximately 25-30 minutes for a full treatment. Turn off the pump and remove the enlarged penis from the cylinder and wash the penis free of lotion. The penis will be 35%-60% longer and with much more girth. Caution, you must not place the penis in any tight underwear or shorts and not dress in tight jeans because the penis development is ongoing for at least one hour and must be allowed to continue to enlarge unimpeded. One should not use the vacuum pump for more than three treatments per week so that the penis has sufficient time to rejuvenate its cells and tissues.

In this world over ten million men suffer from "erectile dysfunction" and shrinking penis size. This significant physical problem is now within reach of being overcome. The key is increasing very low blood pressure by eliminating circulation blockage with contributing low nitrate oxide levels that mostly come with poor eating habits and older age. When there is very low blood circulation a male finds it nearly impossible to obtain a natural erection. Low levels of nitrate oxide are a major reason men cannot achieve a natural erection. By using the preliminary and maintenance formulations containing combinations of selected herbs, vitamins and minerals there is an answer to this problem. The blood vessels must be opened up by removing blockages to allow more circulation of blood which the preliminary formulation will assist in doing. Once that is achieved, the maintenance formulation of selected herbs, vitamins and minerals go to work on restructuring the penis anatomy of the corpora cavernosa and the corpus spongiosum with vital herbs to rejuvenate the cells of this organ that has been neglected, likely for years. With the vacuum pump, preset at the appropriate negative pressure, the penis can be stimulated with the result being the physical change of the penis enlargement in both length and girth dimensions. In this manner the problem of male erectile dysfunction can be virtually eliminated and men can go back to having fun with sexual encounters.

The present invention may be embodied in other specific forms without departing from the spirit or essential attributes thereof and, accordingly, the described embodiments are to be considered in all respects as being illustrative and not restrictive, with the scope of the invention being indicated by the appended claims, rather than the foregoing detailed description, as indicating the scope of the invention as well as all modifications which may fall within a range of equivalency which are also intended to be embraced therein.

The invention claimed is:

1. A method for enhancing penile hemodynamics in humans by increasing the capacity for a natural erection of the male penis comprising the steps of:
   ingesting on a daily basis a preliminary formulation of herbs and vitamins for at least an initial thirty day period prior to treatment of the male penis with a specially configured vacuum pump to increase the blood flow into and through the male penis by reducing plaque deposits and inflammation of the vessels;
   following the initial period, utilizing the vacuum pump having an elongated open-ended cylinder for creating a vacuum over and along the exterior of the male penis to assist in the enlargement of the penis through the engorgement of the tissues of the penis by increased blood flow; and simultaneously with the use of the vacuum pump ingesting on a daily basis a maintenance formulation of a selection of herbs, amino acids, a vitamin, and a mineral to maintain the increased blood flow into and through the male penis, to increase the nitric oxide levels within the human body, to stimulate penile erections, and to rejuvenate and enhance muscle growth and strength of the male penis.

2. The method of claim 1 wherein said preliminary formulation consists of a vitamin for reducing plaque buildup in blood vessels, a first herb for reducing fibrinolytic and antithrombic conditions in the human circulatory and musculature systems, a second herb for assisting against inflammation of blood vessel walls, accompanied by appropriate amounts of water in the range of between 60 and 90 ounces per day depending upon body weight to aid in the dispersal of the formulation throughout the human body.

3. The method of claim 1 wherein said maintenance formulation consists of at least two amino acids, a first herb, and a mineral to assist the human body in manufacturing nitric oxide, at least five selected herbs for rejuvenating and enhancing muscle growth and strength and increasing testosterone level, and a vitamin to continue preventing the build-up of plaque that was previously reduced in the blood vessels.

4. The method of claim 2 wherein the vitamin for reducing plaque buildup in blood vessels is Vitamin E and the recommended dosage is 800 IU/day split equally into two dosages.

5. The method of claim 2 wherein the first herb for reducing fibrinolytic and antithrombic conditions in the human circulatory and musculature systems is triple strength nattozimes and the recommended dosage is four 195 mg. capsules split equally into two dosages.

6. The method of claim 2 wherein the second herb for assisting against inflammation of blood vessel walls is *Aesculus hippocasatanum* and the recommended dosage is two 200 mg. capsules split equally into two dosages.

7. The method of claim 3 wherein the amino acids, a first herb, and a mineral to assist the human body in manufacturing nitric oxide are L-arginine, L-Citrulline, Icariin extract 40% and zinc, the recommended dosages of L-arginine is 6000 mg. daily, L-Citrulline is 3000 mg daily, and Icariin is 500 mg. split equally into two dosages and the recommended dosage of zinc is 75-100 mg. daily.

8. The method of claim 3 wherein the at least five selected herbs for rejuvenating and enhancing muscle growth and strength and increasing testosterone level are *Butea superba*, *Catuaba* bark, *Tongkat ali* extract, *Tribulus terrestris* and Velvet Deer Antler, the recommended dosages are *Butea superba* 500 mg., *Catuaba* bark 465 mg., *Tongkat ali* extract 300 mg., *Tribulus terrestris* 500 mg. and Velvet Deer Antler 500 mg., all split equally into two dosages daily.

9. The method of claim 3 wherein the vitamin to continue preventing the build-up of plaque that was previously reduced in the blood vessels is Vitamin E, the recommended dosage is 800 IU per day split equally into two dosages.

10. An apparatus enhancing penile hemodynamics in humans by increasing the capacity for a natural erection of the male penis comprising:

a vacuum pump having dual inlet ports connected to one of each of two reciprocating vacuum producing valves set to create a pulsating vacuum pressure of a predetermined amount at each of said two vacuum inlet ports;

a T-bar fluid flow path connector attaches to each of the dual vacuum inlet ports creating a single vacuum inlet port;

an elongated open-ended cylinder for creating a vacuum over and along the exterior of the male penis to assist in the enlargement of the penis through the engorgement of the blood vessels of the penis by increased blood flow connected to said single vacuum inlet port of the T-bar connector, said elongated cylinder having an internally smooth surface to receive the male organ for the treatment process and a smooth portal double roll-over flange adapted to create a vacuum seal against the area of the body of the user surrounding the male penis; whereby the elongated cylinder is placed over a flaccid male penis and the vacuum pump is activated creating a temporary vacuum surrounding the male penis causing the penis to elongate and increase girth allowing tissues in the male penis to enlarge and fill with blood resulting in an erection of the penis.

11. The apparatus of claim 10 wherein said elongated cylinder is transparent with a one sixteenth inch outer wall for durability and to prevent cracking or breakage and of sufficient size to accommodate various male organ sizes in a flaccid stage of up to a nine inch length and three inch girth for the development process of the male organ.

12. The apparatus of claim 10 is further comprised of an elongated flexible connecting tube extending between said T-bar connector and said elongated cylinder.

\* \* \* \* \*